(12) United States Patent
Fulgham

(10) Patent No.: US 6,802,316 B1
(45) Date of Patent: Oct. 12, 2004

(54) TRACHEOSTOMY VALVE

(76) Inventor: Charles A. Fulgham, 201 Bedford Dr., Brooklyn, MI (US) 49230

( * ) Notice: Subject to any disclaimer, the term of this patent is extended or adjusted under 35 U.S.C. 154(b) by 340 days.

(21) Appl. No.: 10/144,583

(22) Filed: May 13, 2002

(51) Int. Cl.[7] .............................................. A62B 16/00
(52) U.S. Cl. ............................ 128/207.14; 128/207.15; 128/207.16; 128/207.18
(58) Field of Search ................... 128/207.14, 207.15, 128/207.16, 207.18; 137/855, 852, 527

(56) References Cited

U.S. PATENT DOCUMENTS

| | | | | |
|---|---|---|---|---|
| 3,844,290 A | * | 10/1974 | Birch et al. | 128/207.16 |
| 4,040,428 A | * | 8/1977 | Clifford | 128/207.16 |
| 4,456,016 A | * | 6/1984 | Nowacki et al. | 600/538 |
| 4,596,559 A | * | 6/1986 | Fleischhacker | 604/164.05 |
| 4,614,516 A | * | 9/1986 | Blom et al. | 623/9 |
| 5,059,208 A | * | 10/1991 | Coe et al. | 623/9 |
| 5,391,205 A | * | 2/1995 | Knight | 623/9 |
| 5,505,198 A |   | 4/1996 | Siebens et al. | |
| 6,193,751 B1 | * | 2/2001 | Singer | 623/9 |

* cited by examiner

*Primary Examiner*—Glenn K. Dawson
*Assistant Examiner*—Darwin P. Erezo
(74) *Attorney, Agent, or Firm*—Mary M. Moyne; Ian C. McLeod

(57) ABSTRACT

A tracheostomy valve (10) having a low profile for use on a tracheal tube (100) of a user. The tracheostomy valve is a unidirectional valve which allows gases to enter into the tracheal tube but does not allow gases to exit the tracheal tube through the tracheostomy valve. The valve includes a valve body (12), a flapper valve (24), a valve clamp (26) and a cover (32). The valve body has notches (30) which provide inlets (18) for the gases to move past the valve body. The valve clamp has grooves which provide inlets for the gases to move past the valve clamp into the valve body. The cover mounts over the second end (12B) of the valve body and holds the valve clamp and flapper valve in position in the hole of the valve body.

33 Claims, 4 Drawing Sheets

TRACHEOSTOMY VALVE

CROSS-REFERENCE TO RELATED APPLICATIONS

Not Applicable

STATEMENT REGARDING FEDERALLY SPONSORED RESEARCH OR DEVELOPMENT

Not Applicable

BACKGROUND OF THE INVENTION (1) Field of the Invention

The present invention relates to a tracheostomy valve which prevents air from exiting the tracheostomy tube of a user while allowing air to enter the tracheal tube. In particular, the present invention relates to a tracheostomy valve which is aesthetically pleasing and has a low profile.

(2) Description of the Related Art

The related art has shown various types of unidirectional tracheostomy valves that mount on the end of the tracheal tube, which is inserted into the patient's trachea after a tracheostomy. Such tracheostomy valves allow air to flow through the tracheal tube and into the lungs during inhalation and prevent air from flowing through the tracheal tube during exhalation. Thus, during exhalation, air flows through the patient's upper airways, such as the subglottic trachea, larynx, pharynx, mouth and nasal passages. As a result, tracheotomized individuals using a unidirectional tracheostomy valve are able to communicate orally and maintain clear upper airway passages by coughing or expelling air through the upper airway passages.

U.S. Pat. No. 5,505,198 to Siebens et al describes a tracheostomy valve having a displaceable element, such as a ball, in a chamber. The ball moves about during inhalation and exhalation to open or close an opening in the chamber. However, due to the use of a ball and the size of the ball needed to cover the opening, this device can not be streamlined as with the device of the present invention.

There remains the need for a unidirectional tracheostomy valve which is streamlined with a low profile and which allows a user to inhale through the valve and exhale through the mouth.

SUMMARY OF THE INVENTION

A tracheostomy valve having a low profile for use on a tracheal tube of a user. The tracheostomy valve is a unidirectional valve which allows gases to enter through the tracheostomy valve and into the tracheal tube but does not allow gases to exit the tracheal tube through the tracheostomy valve. The tracheostomy valve enables a user to speak without having to manually block the,tracheal tube. The valve includes a valve body, a flapper valve, a valve clamp and a cover. The construction of the tracheostomy valve allows the tracheostomy valve to have a low profile. The valve body has notches in the perimeter of the sidewall extending the length of the sidewall between the ends of the valve body. The notches provide inlets for the gases to move past the valve body. The valve body has a tubular extension on the first end which is inserted into the opening of the tracheal tube of the user. The valve body has a hole with a first, second and middle section. The middle section is greater in size than the first section and the second section is greater in size than the middle section. Thus, an indention is formed in the second end of the valve body which is in fluid communication with the hole of the valve body, the hole of the tubular extension and the opening of the tracheal tube. The flapper valve is positioned in the second section of the hole in the valve body. The flapper valve has an outer portion connected to an inner portion. The flapper valve is constructed of a thin, flexible material. The valve clamp is also positioned in the second section of the hole of the valve body so that the flapper valve is sandwiched between the first end of the valve clamp and the shoulder formed between the second and middle sections of the hole of the valve body. The valve clamp has a hole which is in fluid communication with the hole of the valve body. The second end of the valve clamp has grooves which extend from the perimeter of the valve clamp to the hole in the valve clamp. The grooves provide inlets for the gases to move past the valve clamp into the hole of the valve clamp and into the hole of the valve body. The cover mounts over the second end of the valve body and holds the valve clamp and flapper valve in position in the second section of the hole of the valve body. The cover can have a decorative second side to increase the aesthetic appearance of the tracheostomy valve. In one (1) embodiment, the valve body and the cover have a cylindrical shape and the cover is screwed onto the valve body.

The valve body has a connector on the first end which allows the tracheostomy valve to be securely connected to the tracheal tube. Once the tracheostomy valve is positioned on the tracheal tube, the user can inhale through the tracheostomy valve. When exhaling, the tracheostomy valve prevents the exit of gases through the tracheostomy valve such that the gases move to the mouth which allows for speech. When a user inhales, the gases adjacent the tracheostomy valve move between the valve body and the sidewall of the cover in the notches in the valve body. The gases then move between the end wall of the cover and the second end of the valve clamp in the grooves of the valve clamp and into the hole of the valve clamp. The gases then move past the open flapper valve. The suction force resulting from the user inhaling and the force of the air moving through the tracheostomy valve, causes the inner portion of the flapper valve to move toward the middle section of the hole of the valve body and away from the outer portion of the flapper valve. This creates an opening between the outer and inner portions of the flapper valve and allows the gases in the hole of the valve clamp to move into the hole in the valve body. Once the gases are in the hole of the valve body, the gases move through the tubular extension and into the tracheal tube and finally to the lungs of the user.

During exhalation, the gases in the lungs move into the tracheal tube through the tubular extension and into the first and middle sections of the hole of the valve body. As the gases attempt to move from the middle section to the second section of the hole, the gases push against the inner portion of the flapper w valve moving the inner portion toward the valve clamp. When the inner portion contacts the valve clamp it blocks the hole in the valve clamp and prevents the gases from moving past the flapper valve. Since the exhaled gases can not escape through the tracheostomy valve, the gases continue to move up the throat of the user past the larynx and into the mouth of the user. Since the air moves past the vocal cords of the user, the user is able to speak without having to remove or adjust the tracheostomy valve.

The present invention relates to a tracheostomy valve for connecting to a tracheal tube, which comprises: a valve body having a first end and a second end with a hole extending between the ends and having an inlet spaced apart from the hole; a tubular extension mounted on the first end of the valve body and extending outward from the first end in a direction opposite the second end and having a hole in fluid communication with the hole of the valve body; a flapper valve positioned adjacent the hole of the valve body on the second end of the valve body and having an outer portion and an inner portion connected together so that the inner portion is able to move while the outer portion remains stationary; a valve clamp having a first end and a second end with a hole extending between the ends and positioned such that the first end of the valve clamp is adjacent the flapper valve and the hole of the valve clamp is in fluid communication with the flapper valve; and a cover positioned adjacent the second end of the valve clamp for connecting to the valve body to hold the valve clamp and the flapper valve adjacent the hole of the valve body wherein in use during inhalation, gases flow into the inlet of the valve body from the first side of the valve body to the second side of the valve body into the hole in the valve clamp, through the flapper valve into the hole of the tubular extension and into the tracheal tube and wherein during exhalation, the flapper valve prevents gases from exiting the tracheal tube through the tracheostomy valve.

Still further, the present invention relates to a tracheostomy valve for attaching to a tracheal tube, which comprises: a valve body having a first end and a second end forming a longitudinal axis of the valve body, with a sidewall and a hole extending between the ends, the hole having a first end and a second end with the first end adjacent the first end of the valve body and the second end adjacent the second end of the valve body and having a first section adjacent the first end, a second section adjacent the second end and a middle section spaced between the first end and the second end and having an inlet in the sidewall spaced apart from the hole; a tubular extension having a first end and a second end with a hole extending between the ends and mounted on the second end to the first end of the hole of the valve body such that the hole of the tubular extension is aligned with the first section of the hole of the valve body wherein the tubular extension is configured to extend into an open end of the tracheal tube; a flapper valve positioned in the second section of the hole of the valve body and having a first portion with a second portion flexibly connected to the first portion wherein the second portion is of a size as to be able to extend into the middle section of the hole of the valve body; a valve clamp having a first end and a second end and positioned in the second section of the hole of the valve body such that the first end is adjacent the flapper valve with a hole extending between the ends and having an inlet extending between a perimeter of the valve clamp and the hole; and a cover connected to the valve body adjacent the second end of the valve body such that the cover holds the valve clamp and flapper valve in the second section of the hole of the valve body wherein in use during inhalation, gases flow into the inlet in the sidewall of the valve body from the first side of the valve body to the second side of the valve body through the inlet in the valve clamp into the hole in the valve clamp, through the flapper valve into the hole of the tubular extension and into the tracheal tube and wherein during exhalation, the flapper valve prevents gases from exiting the tracheal tube through the tracheostomy valve.

Further still, the present invention relates to a method for enabling a user having a tracheal tube to breath and speak which comprises the steps of: providing a trachea valve having a valve body having a first end and a second end with a hole extending between the ends and having an inlet spaced apart from the hole; a tubular extension mounted on the first end of the valve body and extending outward from the first end in a direction opposite the second end and having a hole in fluid communication with the hole of the valve body; a flapper valve positioned adjacent the hole of the valve body on the second end of the valve body and having an outer portion and an inner portion connected together so that the inner portion is able to move while the outer portion remains stationary; a valve clamp having a first end and a second end with a hole extending between the ends and positioned such that the first end of the valve clamp is adjacent the flapper valve and the hole of the valve clamp is in fluid communication with the flapper valve; and a cover positioned adjacent the second end of the valve clamp for connecting to the valve body to hold the valve clamp and the flapper valve adjacent the hole of the valve body; connecting the trachea valve to an opening of the tracheal tube; inhaling such that gases adjacent the trachea valve move into the trachea valve through the inlet of the valve body into the hole in the valve clamp through the flapper valve into the hole of the valve body and into the opening of the tracheal tube; and exhaling such that gases in the lungs move through the trachea tube into the hole of the valve body and are prevented from exiting the trachea valve by the flapper valve such that the gases move to a mouth of the user such as to allow a user to speak.

The substance and advantages of the present invention will become increasingly apparent by reference to the following drawings and the description.

BRIEF DESCRIPTION OF THE DRAWINGS(S)

Figure 1:
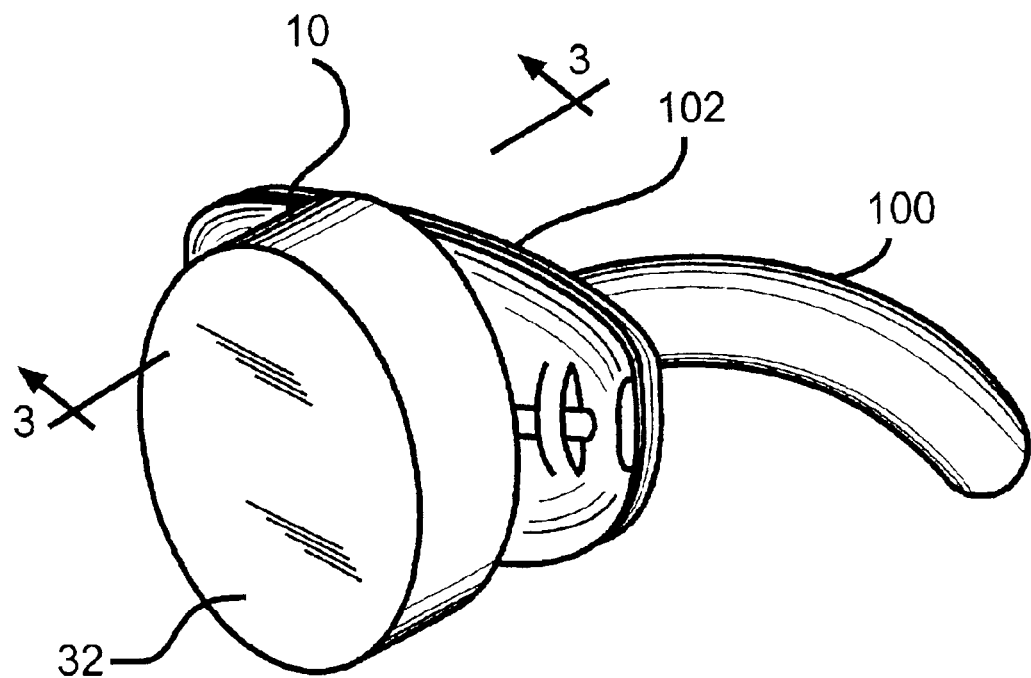
FIG. 1 is a perspective view of the tracheostomy valve 10 mounted on a tracheal tube 100.
Figure 3:
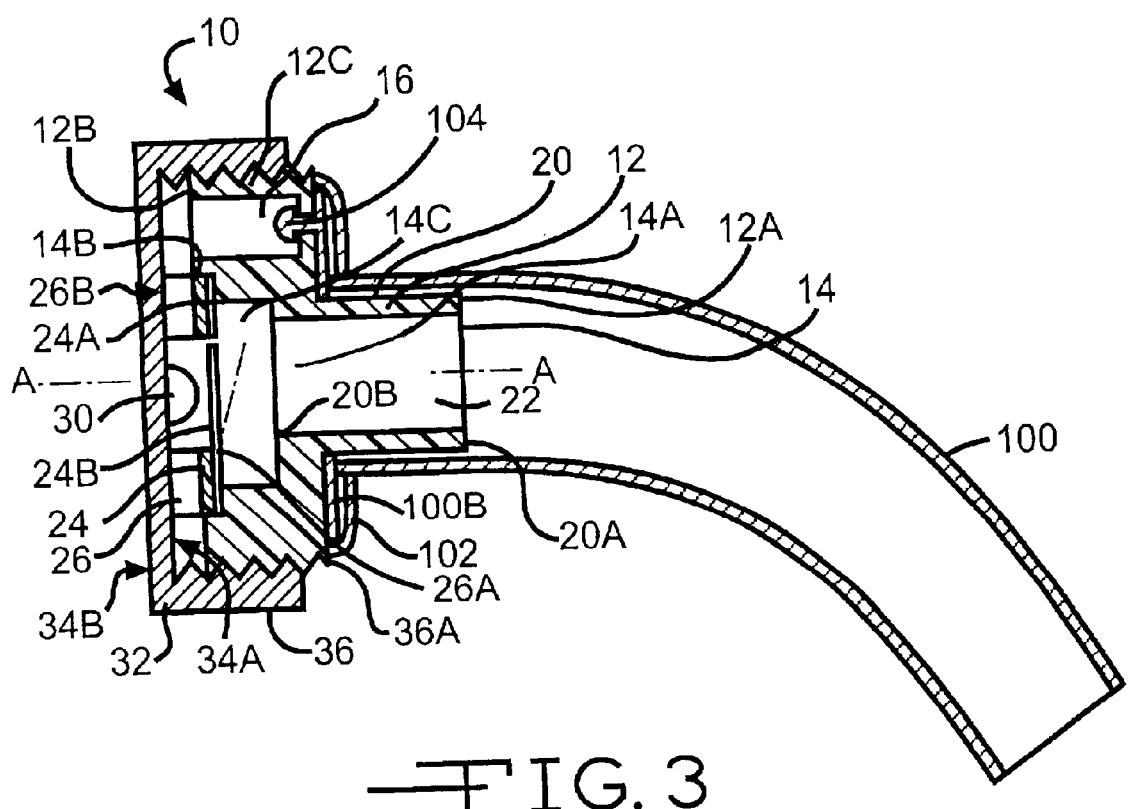

FIG. 3 is a cross-sectional view along the line 3—3 of FIG. 1 showing the valve body 12, the hole 14, the flapper valve 24 and the valve clamp 26.

Figure 4:
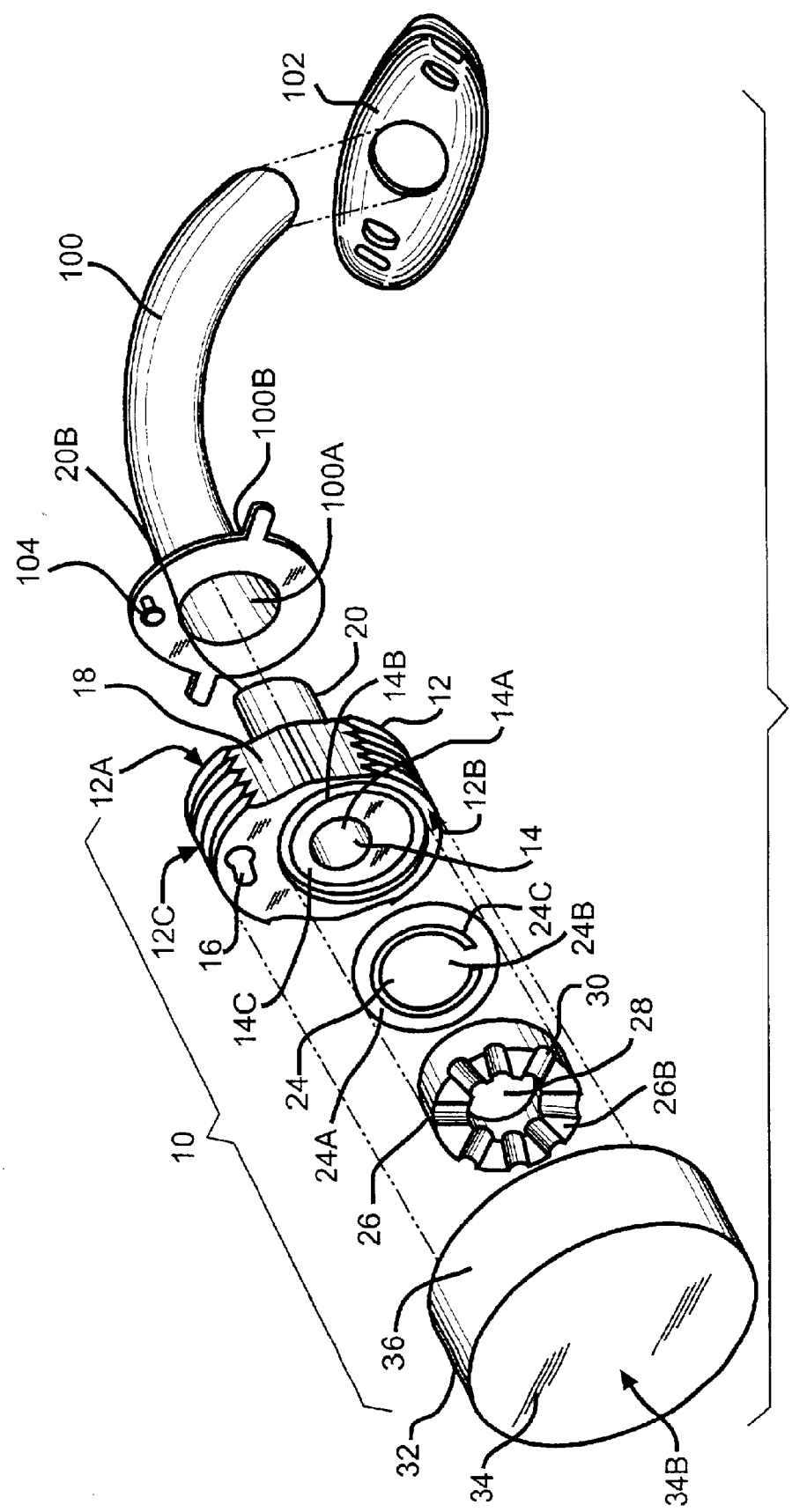

FIG. 4 is an exploded view of the tracheostomy valve 10 showing the cover 32, the valve clamp 26, the flapper valve 24, the valve body 12, the tracheal tube 100 and the neck plate 102.

Figure 4A:
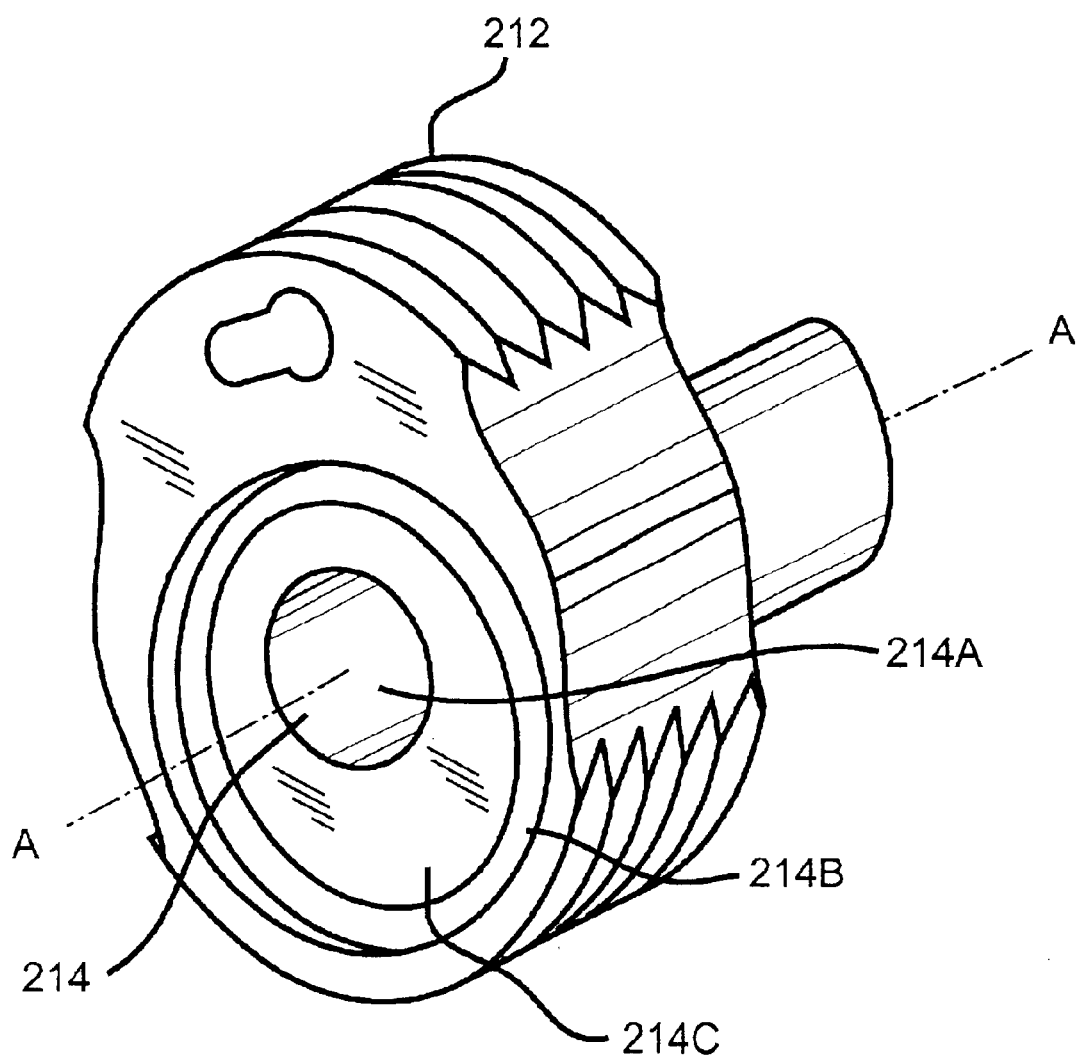

FIG. 4A is a partial view of the valve body 212 of an alternate embodiment.

DESCRIPTION OF THE PREFERRED EMBODIMENT(S)

Figure 2:
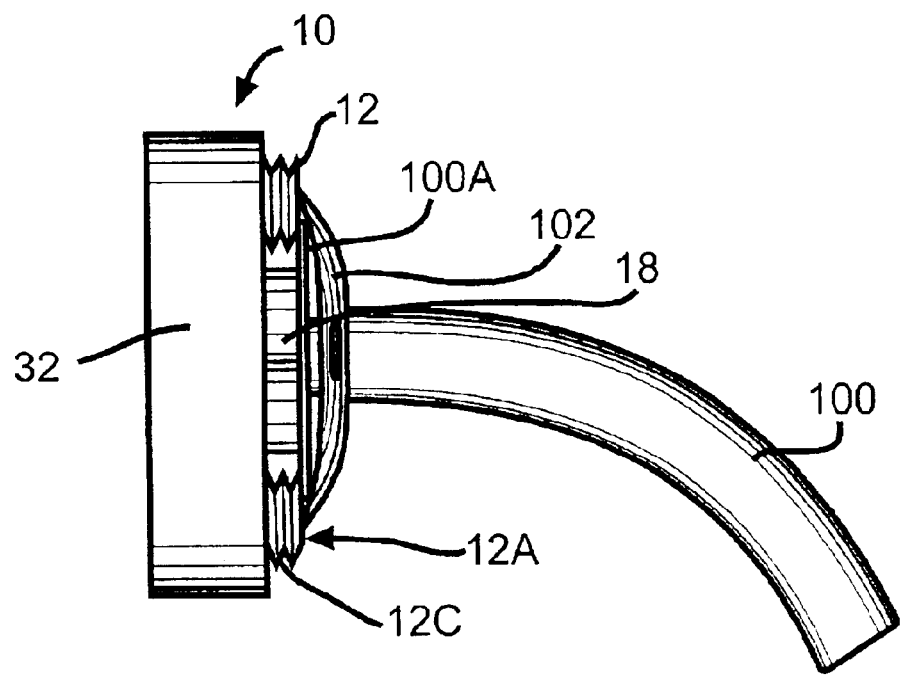
FIG. 2 is a side view of the tracheostomy valve 10 mounted on the tracheal tube 100.

The tracheostomy valve 10 of the present invention is intended to be secured into the end of a tracheal tube 100 of a user (FIGS. 1 and 2). The tracheal tube 100 is inserted into the tracheostomy opening (not shown) created in the trachea during a tracheotomy. The tracheostomy valve 10 is a unidirectional valve which allows a user to inhale through the tracheostomy valve 10 while preventing the exhalation of air through the valve 10 such that the user is able to speak without having to manually block the tracheal tube 100.

The tracheostomy valve 10 includes a valve body 12, a flapper valve 24, a valve clamp 26 and a cover 32 (FIG. 4). The valve body 12 has a first and second end 12A and 12B forming a longitudinal axis A—A of the valve body 12 with a hole 14 extending between the ends 12A and 12B. In one (1) embodiment, the hole 14 is aligned with the longitudinal axis A—A of the valve body 12. The hole 14 has a first section 14A, a second section 14B and a middle section 14C all in fluid communication. The first section 14A extends from the first end 12A of the valve body 12 to the middle section 14C of the hole 14. The middle section 14C of the hole 14 extends between the first section 14A and the second section 14B. The middle section 14C preferably has a size greater than the size of the first section 14A. The second section 14B of the hole 14 extends from the middle section 14C to the second end 12B of the valve body 12. In one (1) embodiment, the second section 14B has a shape similar to the shape of the middle section 14C. The size of the second section 14B is greater than the size of the middle section 14C such that a shoulder or ledge is formed between the middle section 14C and the second section 14B. The size of the hole 14 depends on the amount of air needed to be inhaled by the user. Thus, the size of the hole 14 in the valve body 12 generally depends on the size of the user. In one (1) embodiment, the valve body 12 has an essentially cylindrical shape and the hole 14 including the first, second and middle sections 14A, 14B and 14C is a bore with all sections 14A, 14B and 14C having a circular cross-section. In this embodiment, the hole 14 is coaxial with the valve body 12.

In an alternate embodiment, the centerlines of the middle and second sections 214C and 214B of the hole 214 of the valve body 212 are offset from the centerline of the first section 214A of the hole 214 (FIG. 4A). In the embodiment where the first section 214A of the hole 214 is coaxial with the longitudinal axis A-A of the valve body 212, the centerline of the middle and second sections 214C and 214B are offset from the longitudinal axis A-A of the valve body 212. In one (1) embodiment, the second section 214B is aligned and coaxial with the middle section 214C. In this embodiment, when the tracheostomy valve is positioned on the tracheal tube 100 which is positioned in a user, the second and middle sections 214B and 214C of the hole 214 are offset downward in a direction away from the user's mouth. In this embodiment, the first section 214A of the hole 214 has a diameter of 0.312 inch (0.792 cm) and is coaxial with the valve body 212. The centerlines of the middle section 214C and second section 214B of the hole 214 are offset from the longitudinal axis A—A of the valve body 212 by approximately 0.11 inch (0.30 cm).

The valve body 12 has a connector 16 to attach the valve body 12 and the valve 10 to the end of the tracheal tube 100. The connector 16 is provided on the first end 12A spaced apart from the hole 14 of the valve body 12. The tracheal tube 100 may be provided with a collar 100B at the open end of the tracheal tube 100. The collar 100B extends around the perimeter of the open end of the tracheal tube 100. The collar 100B may have tongs which are inserted into openings in a neck plate 102 to secure the neck plate 102 to the collar 100B and the tracheal tube 100. The neck plate 102 is well known in the art and protects the user's tracheal opening 100A. The collar 100B of the tracheal tube 100 has a fastener 104 which connects with the connector 16 on the first end 12A of the valve body 12. In one (1) embodiment, the fastener 104 is a bayonet fastener or a rotation lock and the connector 16 is a key shaped opening into which the bayonet fastener or rotation lock is inserted. In this embodiment, the valve body 12 is fastened onto the collar 100B body by rotating the valve body 12 about its longitudinal axis A-A such that the fastener 104 is secured in the connector 16 of the valve body 12. It is understood that the valve body 12 can be secured to the tracheal tube 100 by any well known means.

An inlet 30 is provided in the valve body 12. The inlet 30 extends between the ends 12A and 12B of the valve body 12. In one (1) embodiment, the inlet 30 is formed by a notch 30 in the sidewall 12C of the valve body 12. In one (1) embodiment, the valve body 12 has two (2) notches 30. The notches 30 are provided such as to not interfere with the hole 14 of the valve body 12 or the connector 16 of the valve body 12. The size of the notches 30 depends on the amount of air needed to be moved through the valve 10. The inlet 30 could also be provided by openings (not shown) extending through the sidewall 12C of the valve body 12 between the ends 12A and 12B.

A tubular extension 20 having opposed ends 20A and 20B with a hole 22 extending between the ends 20A and 20B is mounted on the first end 12A of the valve body 12 and extends outward away from the valve body 12. One (1) end 20A of the tubular extension 20 is mounted on the opening of the hole 14 in the first end 12A of the valve body 12 such that the hole 22 of the tubular extension 20 is in fluid communication with the hole 14 of the valve body 12. In one (1) embodiment, the size and shape of the hole 22 of the tubular extension 20 are similar to the size and shape of the first section 14A of the hole 14 of the valve body 12. In one (1) embodiment, the first section 14A of the hole 14 of the valve body 12 and the hole 22 of the tubular extension 20 have a circular cross-section and the tubular extension 20 is coaxial with the first section 14A of the hole 14 of the valve body 12. The end 20B of the tubular extension 20 opposite the valve body 12 has a size and shape which allows the tubular extension 20 to be inserted into the opening 100A of the tracheal tube 100. The valve body 12 and the tubular extension 20 can be constructed as a unitary piece. In one (1) embodiment, the valve body 12 and tubular extension 20 are constructed of plastic such as Acetron.

A flapper valve 24 is positioned in the second section 14B of the hole 14 of the valve body 12 on the shoulder adjacent the middle section 14C of the hole 14. The flapper valve 24 preferably has the same outer shape as the second section 14B of the hole 14 of the valve body 12. The size of the flapper valve 24 is slightly less than the size of the second section 14B of the hole 14 such that the flapper valve 24 can be easily positioned in the second section 14B of the hole 14. In one (1) embodiment, the flapper valve 24 has a circular shape. The flapper valve 24 has an outer portion 24A and an inner portion 248. The outer portion 24A is flexibly connected to the inner portion 24B such that the outer portion 24A can remain stationary when the inner portion 24B moves. In one (1) embodiment, the flapper valve 24 is constructed from a single sheet of material. The flapper valve 24 has a slot 24C which is cut around most of the perimeter of the flapper valve 24 but spaced apart from the perimeter of the flapper valve 24. The slot 24C separates the center or inner portion 24B of the flapper valve 24 from the outer section 24A of the flapper valve 24. In one (1) embodiment, the inner portion 24B has a shape similar to the outer portion 24A. The size of the inner portion 24B of the flapper valve 24 is preferably less than the size of the middle section 14C of the hole 14 such that the inner portion 24B can extend into the middle section 14C of the hole 14. The shape of the inner portion 24B of the flapper valve 24 is preferably similar to the shape of the middle section 14C of the hole 14. In one (1) embodiment, the middle section 14C has a circular cross-section and the inner portion 24B of the flapper valve 24 has an essentially circular shape. In one (1) embodiment, the flapper valve 24 has a thickness of 0.008 to 0.010 inches (0.020 to 0.025 cm). The flapper valve 24 can be constructed of any well known flexible material such as vinyl.

The valve clamp 26 has a first and second end 26A and 26B with a hole 28 extending between the ends 26A and 26B. In one (1) embodiment, the valve clamp 26 has a cylindrical shape and the hole 28 is a bore extending through the center of the valve clamp 26. The valve clamp 26 is positioned in the second section 14B of the hole 14 of the valve body 12 adjacent the flapper valve 24 such that the flapper valve 24 is sandwiched or seated between the shoulder formed between the middle and second sections 14C and 14B of the hole 14 and the first end 26A of the valve clamp 26. In one (1) embodiment, the valve clamp 26 has the same outer perimeter shape as the flapper valve 24. In one (1) embodiment, the valve clamp 26 has the same outer shape as the second section 14B of the hole 14 of the valve body 12. In this embodiment, the outer diameter of the valve clamp 26 is slightly less than the diameter of the second section 14B of the hole 14 of the valve body 12 such that the valve clamp 26 is easily positioned in the hole 14 without allowing extraneous side-to-side movement. The size of the valve clamp 26 is greater than the size of the middle section 14C of the hole 14 of the valve body 12 such that the valve clamp 26 rests on the shoulder formed between the middle and second sections 14C and 14B of the hole 14 and does not extend into the middle section 14C of the hole 14. The length of the valve clamp 26 between the ends 26A and 26B is greater than the length or depth of the second section 14B of the hole 14. Thus, when the valve clamp 26 is positioned in the second section 14B of the hole 14, the second end 26B of the valve clamp 26 extends beyond the second end 12B of the valve body 12. In the embodiment where the hole 28 is a bore extending through the center of the valve clamp 26, the valve clamp 26 is positioned in the second section 14B of the hole 14 of the valve body 12 such that the hole 28 is coaxial with the second and middle sections 14B and 14C of the hole 14. The second end 26B of the valve clamp 26 is provided with inlets or passageways 30 which extend from the perimeter of the valve clamp 26 to the hole 28 in the valve clamp 26. In one (1) embodiment, the inlets 30 are grooves cut in the second end 26B of the valve clamp 26. However, it is understood that the inlet or passageways 30 could be provided by other means such as holes extending through the sidewall of the valve clamp 26 from the perimeter to the hole 28. The number of grooves 30 in the valve clamp 26 depends on the size of the tracheal tube 100. To determine the number of grooves 30 needed in the valve clamp 26 to provide the necessary amount of air flow, the area of the hole 28 of the valve clamp 26 and the area of a single groove 30 of the valve clamp 26 are calculated. In one (1) embodiment, the area of the hole 22 of the tubular extension 20 and the area of the first section 14A of the hole 14 of the valve body 12 and the area of the hole 28 of the valve clamp 26 are essentially equal. The area of the hole 28 of the valve clamp 26 is divided by the area of the single groove 30 of the valve clamp 26. In one (1) embodiment where the valve clamp 26 is cylindrical, the hole 22 has a diameter of 0.312 inch (0.792 cm) and there are eight (8) grooves having a radius of 0.078 inch (0.198 cm) evenly spaced about the second end 26B around the hole 28. In one (1) embodiment, the valve clamp 26 is constructed of plastic such as Acetron. However, it is understood that the valve clamp 26 could be constructed of any durable, lightweight material.

The cover 32 is provided for mounting over the second end 12B of the valve body 12. The cover 32 acts to hold the valve clamp 26 and the flapper valve 24 in the hole 14 in the valve body 12. The cover 32 has an end wall 34 having a first and second side 34A and 34B, with a sidewall 36 extending outward from the first side 34A around the perimeter of the end wall 34. The shape of the end wall 34 of the cover 32 is preferably similar to the outer shape of the valve body 12 without the inlets 30. The cover 32 is positioned on the valve body 12 such that the first side 34A of the end wall 34 is adjacent the second end 12B of the valve body 12 and the second end 26B of the valve clamp 26 with the sidewall 36 extending along the sides of the valve body 12. The cover 32 can be secured on the valve body 12 by any well known means. The cover 32 is positioned on the valve body 12 such that the first side 34A of the end wall 34 of the cover 32 contacts the second end 26B of the valve clamp 26 such that the end wall 34 of the cover 32 is spaced apart from the second side 14B of the valve body 12. In one (1) embodiment, the first end 12A of the valve body 12 extends beyond the end of the sidewall 36 of the cover 32 when the cover 32 is positioned fully on the valve body 12. In one (1) embodiment, the valve body 12 has an essentially cylindrical shape with the outer surface of the sidewall 12C of the valve body 12 provided with threads and the outer cover 32 has a cylindrical shape with threads on the inner surface 36A of the sidewall 36. The cover 32 is threaded onto the valve body 12. However, the cover 32 could be constructed of any well known material such as metals or plastics. In one (1) embodiment, the cover 32 is constructed of stainless steel. The second side of the cover 32 can have a decorative design to make the tracheostomy valve 10 more aesthetic.

The tracheostomy valve 10 is connected to the open end of the user's tracheal tube 100. In one (1) embodiment, the tracheostomy valve 10 is connected to the collar 100B of the tracheal tube 100 by a rotating lock. In this embodiment, the direction of rotation needed to lock the tracheal tube 100 on the collar 100B is preferably the same direction of rotation to secure the cover 32 on the valve body 12. To use the tracheostomy valve 10, the user inhales such that the air and other gases adjacent the valve 10 move into the inlets 18 of the valve body 12 from the first end 12A of the valve body 12 to the second end 12B of the valve body 12. In the embodiment where the inlets 18 are provided by notches in the outer surface of the sidewall 12C of the valve body 12, the gases move through the notches 30 which form passageways between the sidewall 12C of the valve body 12 and the sidewall 36 of the cover 32. The air then moves through the inlets 30 in the valve clamp 26 to the hole 28 in the valve clamp 26. In one (1) embodiment where the inlets 30 are formed by grooves in the second side of the valve clamp 26, the gases move through the grooves between the first side 34A of the end wall 34 of the cover 32 and the valve clamp 26. The air moves through the hole 28 in the valve clamp 26 and through the open flapper valve 24. The suction force on the inner portion 24B of the flapper valve 24 caused by the inhalation of the user, causes the inner portion 24B of the flapper valve 24 to move into the middle section 14C of the hole 14 which opens a passageway through the flapper valve 24 (FIG. 3). The length or depth of the middle section 14C of the hole 14 allows the inner portion 24B of the flapper valve 24 to move inward without blocking the first section 14A of the hole 14. In one (1) embodiment, the flapper valve 24 is initially in the open position with the inner portion 24B extending into the middle section 14C of the hole 14. In one (1) embodiment, when the tracheostomy valve 10 is positioned on the tracheal tube 100 of the user, the flapper valve 24 is positioned in the second section 14B of the hole 14 of the valve body 12 such that the connector 16 of the inner and outer portions 24B and 24A of the flapper valve 24 is at the low point or bottom of the valve 24 and the inner portion 24B is bent inward and downward when in the open position. The gases move past the flapper valve 24, through the first section 14A of the hole 14, through the hole 22 of the tubular extension 20 and into the tracheal tube 100 of the user. The inhaled gases then move to the lungs of the user. It is understood that the size and number of grooves in the valve body 12, the size and number of grooves in the valve clamp 26, the size of the hole 22 of the tubular extension 20, the size of the hole 14 in the valve body 12 and the size of the hole 28 of the valve clamp 26 depends on the amount of gases needed to be inhaled through the tracheostomy valve 10.

When exhaling, the gases in the user's lungs move up the trachea of the user to the tracheal tube 100. The gases move from the tracheal tube 100 through the hole 22 in the tubular extension 20 and into the first section 14A of the hole 14 in the valve body 12. As the gases enter the middle section 14C of the hole 14 of the valve body 12, the gases encounter the inner portion 24B of the flapper valve 24. The force of the gases on the inner portion 24B of the flapper valve 24 move the flapper valve 24 toward the second section 14B of the hole 14 and toward the valve clamp 26 (FIG. 3). The inner portion 24B of the flapper valve 24 contacts the first side of the valve clamp 26 and blocks the hole 28 in the valve clamp 26. The size of the inner portion 24B of the flapper valve 24 is greater than the size of the hole 28 of the valve clamp 26 such that the inner portion 24B blocks the hole 28. In one (1) embodiment where the hole 28 is circular and has a diameter of approximately 0.312 inch (0.792 cm), the inner portion 24B of the flapper valve 24 is circular and has a diameter of approximately 0.5 inch (1.27 cm). Thus, in this position, the flapper valve 24 is closed and the inner portion 24B of the flapper valve 24 prevents the gases in the hole 14 of the valve body 12 from exiting the valve body 12. Since the gases are prevented from exiting through the tracheal tube 100, the gases continue up the user's throat past the user's larynx and into the user's mouth. The exhaled gases can be used to allow a user to speak.

The tracheostomy valve 10 enables the user to inhale and speak without having to adjust the valve 10. In addition, due to the construction of the tracheostomy valve 10, the tracheostomy valve 10 has a very small and streamlined shape with a very flat, low profile. In one (1) embodiment, the tracheostomy valve 10 without the extension 20 has a width of approximately 0.375 inch (0.953 cm) and has a diameter of approximately 1.25 inch (3.18 cm). Thus, the user is able to easily hide or disguise the valve 10.

It is intended that the foregoing description be only illustrative of the present invention and that the present invention be limited only by the hereinafter appended claims.

I claim:

1. A tracheostomy valve for connecting to a tracheal tube, which comprises:
   (a) a valve body having a first end and a second end with a hole extending between the ends and having an inlet spaced apart from the hole;
   (b) a tubular extension mounted on the first end of the valve body and extending outward from the first end in a direction opposite the second end and having a hole in fluid communication with the hole of the valve body;
   (c) a flapper valve positioned adjacent the hole of the valve body on the second end of the valve body and having an outer portion and an inner portion connected together so that the inner portion is able to move while the outer portion remains stationary;
   (d) a valve clamp having a first end and a second end with a hole extending between the ends and positioned such that the first end of the valve clamp is adjacent the flapper valve and the hole of the valve clamp is in fluid communication with the flapper valve; and
   (e) a cover positioned adjacent the second end of the valve clamp for connecting to the valve body to hold the valve clamp and the flapper valve adjacent the hole of the valve body wherein in use during inhalation, gases flow into the inlet of the valve body from the first side of the valve body to the second side of the valve body into the hole in the valve clamp, through the flapper valve into the hole of the tubular extension and into the tracheal tube and wherein during exhalation, the flapper valve prevents gases from exiting the tracheal tube through the tracheostomy valve.

2. The valve of claim 1 wherein the cover has an end wall having a first side and a second side with a sidewall extending outward from the first side in a direction opposite the second side and wherein the cover is fastened on the valve body such that the first side of the end wall is adjacent the second side of the valve body and the second side of the valve clamp and the sidewall of the cover extends along sides of the valve body.

3. The valve of claim 2 wherein the valve body has an essentially cylindrical shape with threads provided in the sides and wherein an inner side of the sidewall of the cover has threads which mate with the threads in the sides of the valve body to fasten the cover onto the valve body.

4. The valve of claim 1 wherein the first end of the valve body is provided with a connector which connects the valve body to the tracheal tube.

5. The valve of claim 1 wherein the inlet is provided by a groove extending between the ends of the valve body in a perimeter of the valve body.

6. The valve of claim 1 wherein the flapper valve is constructed of a thin, flexible material.

7. The valve of claim 1 wherein the outer portion of the flapper valve surrounds a perimeter of the inner portion of the flapper valve.

8. The valve of claim 7 wherein a size of the inner portion of the flapper valve is less than a size of an opening of the hole in the second end of the valve body such that the inner portion of the flapper valve is able to extend into the opening of the hole and wherein a size of the outer portion of the flapper valve is greater than the size of the opening of the hole in the second end of the valve body such that the outer portion of the flapper valve can not extend into the opening.

9. The valve of claim 1 wherein the valve clamp has an inlet which extends between a perimeter of the valve clamp and the hole of the valve clamp.

10. The valve of claim 9 wherein the inlet of the valve clamp is provided by a groove in the second side of the valve clamp extending from the perimeter of the valve clamp to the hole of the valve clamp.

11. The valve of claim 10 wherein a plurality of grooves are provided in the second side of the valve clamp to provide the inlet for the valve clamp.

12. The valve of claim 1 wherein a size of the hole in the valve clamp is less than a size of the outer portion of the flapper valve.

13. A tracheostomy valve for attaching to a tracheal tube, which comprises:
   (a) a valve body having a first end and a second end forming a longitudinal axis of the valve body, with a sidewall and a hole extending between the ends, the hole having a first end and a second end with the first end adjacent the first end of the valve body and the second end adjacent the second end of the valve body and having a first section adjacent the first end, a second section adjacent the second end and a middle section spaced between the first end and the second end and having an inlet in the sidewall spaced apart from the hole;

(b) a tubular extension having a first end and a second end with a hole extending between the ends and mounted on the second end to the first end of the hole of the valve body such that the hole of the tubular extension is aligned with the first section of the hole of the valve body wherein the tubular extension is configured to extend into an open end of the tracheal tube;

(c) a flapper valve positioned in the second section of the hole of the valve body and having a first portion with a second portion flexibly connected to the first portion wherein the second portion is of a size as to be able to extend into the middle section of the hole of the valve body;

(d) a valve clamp having a first end and a second end and positioned in the second section of the hole of the valve body such that the first end is adjacent the flapper valve with a hole extending between the ends and having an inlet extending between a perimeter of the valve clamp and the hole; and (e) a cover connected to the valve body adjacent the second end of the valve body such that the cover holds the valve clamp and flapper valve in the second section of the hole of the valve body wherein in use during inhalation, gases flow into the inlet in the sidewall of the valve body from the first side of the valve body to the second side of the valve body through the inlet in the valve clamp into the hole in the valve clamp, through the flapper valve into the hole of the tubular extension and into the tracheal tube and wherein during exhalation, the flapper valve prevents gases from exiting the tracheal tube through the tracheostomy valve.

14. The valve of claim 13 wherein a center of the first section of the hole of the valve body is coaxial with the longitudinal axis of the valve body.

15. The valve of claim 13 wherein the cover has an end wall having a first side and a second side with a sidewall extending outward from the first side in a direction opposite the second side and wherein the cover is fastened on the valve body such that the first side of the end wall is adjacent the second side of the valve body and the second side of the valve clamp and the sidewall of the cover extends along an outer surface of the sidewall of the valve body.

16. The valve of claim 15 wherein the second side of the cover has a decorative design.

17. The valve of claim 15 wherein the valve body has an essentially cylindrical shape with threads provided in the outer surface of the sidewall and wherein an inner side of the sidewall of the cover has threads which mate with the threads in the sidewall of the valve body to fasten the cover on the valve body.

18. The valve of claim 13 wherein the inlet of the valve body is provided by a groove extending between the ends of the valve body in an outer surface of the sidewall of the valve body.

19. The valve of claim 15 wherein there are two grooves in the outer surface of the sidewall which provide the inlet for the valve body.

20. The valve of claim 13 wherein a size of the middle section of the hole of the valve body is greater than a size of the first section of the hole.

21. The valve of claim 20 wherein a size of the second section of the hole of the valve body is greater than a size of the middle section of the hole.

22. The valve of claim 13 wherein the flapper valve is constructed of a thin, flexible material.

23. The valve of claim 13 wherein the first portion of the flapper valve surrounds a perimeter of the middle section of the hole of the valve body.

24. The valve of claim 13 wherein an outer perimeter size of the first portion of the flapper valve is essentially equal to a size of the second section of the hole of the valve body.

25. The valve of claim 13 wherein the inlet of the valve clamp is provided by a groove in the second side of the valve clamp extending from the perimeter of the valve clamp to the hole of the valve clamp.

26. The valve of claim 25 wherein a plurality of grooves are provided in the second side of the valve clamp to provide the inlet for the valve clamp.

27. The valve of claim 13 wherein a length of the valve clamp between the ends is greater than a length of the second section of the hole of the valve body such that when the valve clamp is positioned in the second section of the hole, the second end of the valve clamp extends beyond a second end of the valve body in a direction opposite the first end of the valve body so that when the cover is mounted on the valve body, the cover contacts the second side of the valve clamp and is spaced apart from the second side of the valve body.

28. The valve of claim 13 wherein an outer shape of the valve clamp is essentially similar to a shape of the second section of the hole of the valve body.

29. The valve of claim 28 wherein the valve clamp and the second section of the hole of the valve body have an essentially cylindrical shape and wherein an outer diameter of the valve clamp is slightly smaller than a diameter of the second section of the hole such that the valve clamp is easily positioned in the second section of the hole.

30. The valve of claim 13 wherein the first end of the valve body is provided with a connector which connects the valve body to the tracheal tube.

31. The valve of claim 13 wherein the hole of the valve body is coaxial with the longitudinal axis of the valve body.

32. The valve of claim 1 wherein the valve body and the tubular extension are a unitary piece.

33. A method for enabling a user having a tracheal tube to breath and speak which comprises the steps of:

(a) providing a trachea valve having a valve body having a first end and a second end with a hole extending between the ends and having an inlet spaced apart from the hole; a tubular extension mounted on the first end of the valve body and extending outward from the first end in a direction opposite the second end and having a hole in fluid communication with the hole of the valve body; a flapper valve positioned adjacent the hole of the valve body on the second end of the valve body and having an outer portion and an inner portion connected together so that the inner portion is able to move while the outer portion remains stationary; a valve clamp having a first end and a second end with a hole extending between the ends and positioned such that the first end of the valve clamp is adjacent the flapper valve and the hole of the valve clamp is in fluid communication with the flapper valve; and a cover positioned adjacent the second end of the valve clamp for connecting to the valve body to hold the valve clamp and the flapper valve adjacent the hole of the valve body;

(b) connecting the trachea valve to an opening of the tracheal tube;

(c) inhaling such that gases adjacent the trachea valve move into the trachea valve through the inlet of the valve body into the hole in the valve clamp through the flapper valve into the hole of the valve body and into the opening of the tracheal tube; and (d) exhaling such that gases in the lungs move through the trachea tube into the hole of the valve body and are prevented from exiting the trachea valve by the flapper valve such that the gases move to a mouth of the user such as to allow a user to speak.

* * * * *